United States Patent
Hessert et al.

(10) Patent No.: US 7,649,620 B2
(45) Date of Patent: Jan. 19, 2010

(54) METHOD AND SYSTEM FOR SYNCHRONISING ANGLES

(75) Inventors: Roland Hessert, Markt Indersdorf (DE);
Wilhelm Satzger, Munich (DE);
Juergen Bosse, Fuerstenfeldbruck (DE);
Bernhard Thaler, Eichenau (DE)

(73) Assignee: MTU Aero Engines GmbH, Munich (DE)

( * ) Notice: Subject to any disclaimer, the term of this patent is extended or adjusted under 35 U.S.C. 154(b) by 428 days.

(21) Appl. No.: 11/665,143

(22) PCT Filed: Oct. 7, 2005

(86) PCT No.: PCT/DE2005/001793

§ 371 (c)(1),
(2), (4) Date: Apr. 10, 2007

(87) PCT Pub. No.: WO2006/042504

PCT Pub. Date: Apr. 27, 2006

(65) Prior Publication Data

US 2008/0084566 A1 Apr. 10, 2008

(30) Foreign Application Priority Data

Oct. 15, 2004 (DE) .................. 10 2004 050 426

(51) Int. Cl.
*G01C 1/00* (2006.01)
(52) U.S. Cl. ....................... 356/138; 901/47
(58) Field of Classification Search ................ 356/138, 356/139.08, 141.4; 901/47
See application file for complete search history.

(56) References Cited

U.S. PATENT DOCUMENTS 4,714,339 A    12/1987  Lau et al.

(Continued)

FOREIGN PATENT DOCUMENTS

| DE | 199 20 458 | 11/2000 |
| DE | 199 53 114 | 5/2001 |
| EP | 1 459 834 | 12/2007 |

OTHER PUBLICATIONS

Ishida et al., "Two arc welding robots coordinated with 3-D vision sensor", Control and Instrumentation, 1994, IECON '94, 20$^{th}$ International Conference on Bologna, Italy, Sep. 5-9, 1994, vol. 2, 5. Sep. 5, 1994, pp. 830 to 834, XP010137569, ISBN: 0-7803-1328-3.

(Continued)

*Primary Examiner*—Roy Punnoose
(74) *Attorney, Agent, or Firm*—Davidson, Davidson & Kappel, LLC

(57) ABSTRACT

A method and a system for synchronising angles of at least two displaceable working means (2, 2') at a predetermined point of action (4) is disclosed. The working means are, in particular, a robot-controlled tool or a robot-controlled radiation emitter and/or radiation receiver. In order to synchronise angles in a precise manner, the directions of the action (1, 1') of the working means (2, 2') are, in particular represented in a continuous manner, detected and united at a predetermined point of action (4). The angle (a) between the directions of the action (1, 1') of the working means (2, 2') is determined by, in particular, an optical angle measurement and is adjusted to a predetermined value.

21 Claims, 1 Drawing Sheet

U.S. PATENT DOCUMENTS

| | | | | |
|---|---|---|---|---|
| 5,346,030 | A | * | 9/1994 | Ohmura et al. ............. 180/412 |
| 5,661,551 | A | * | 8/1997 | Yamabuchi ................ 356/5.01 |
| 5,875,726 | A | | 3/1999 | Keilmann |
| 5,898,482 | A | * | 4/1999 | Yamabuchi ................ 356/4.01 |
| 6,435,715 | B1 | | 8/2002 | Betz et al. ................... 378/197 |
| 2004/0059486 | A1 | * | 3/2004 | Takuma et al. ................ 701/41 |
| 2004/0093119 | A1 | | 5/2004 | Gunnarsson et al. |

OTHER PUBLICATIONS

Decker et al., "Dynamic Measurement of Position and Orientation of Robots", IEEE Transactions on Instrumentation and Measurement, IEEE inc., vol. 41, No. 6, Dec. 1, 1992, pp. 897-901, XP000358664, ISSN: 0018-9456.

* cited by examiner

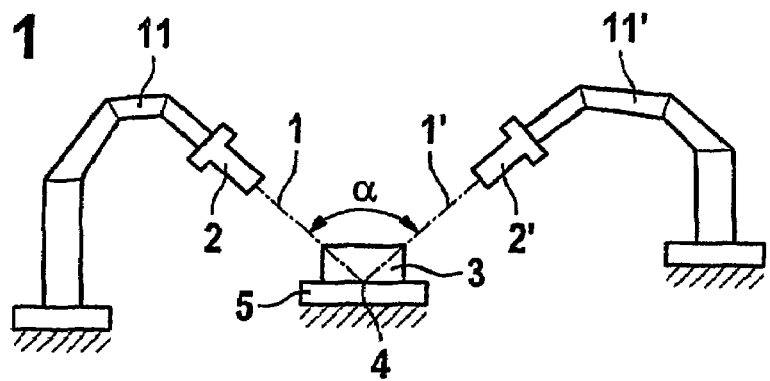
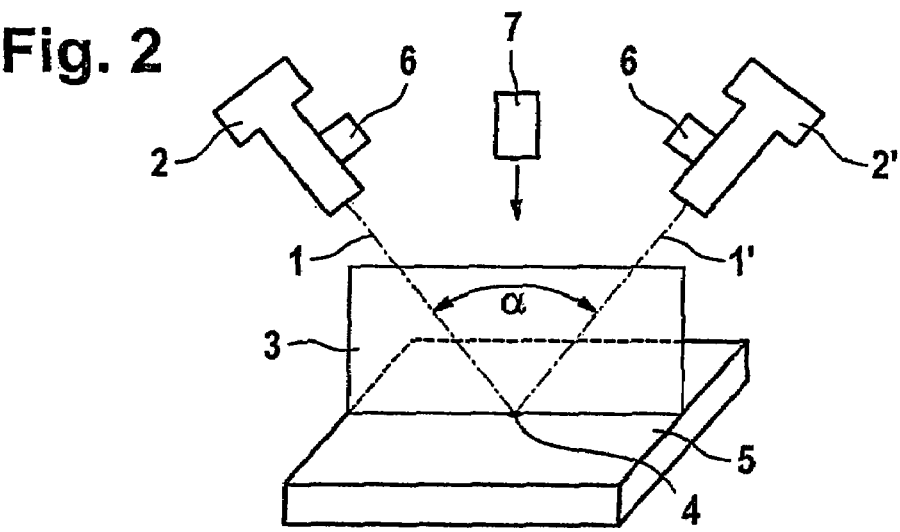
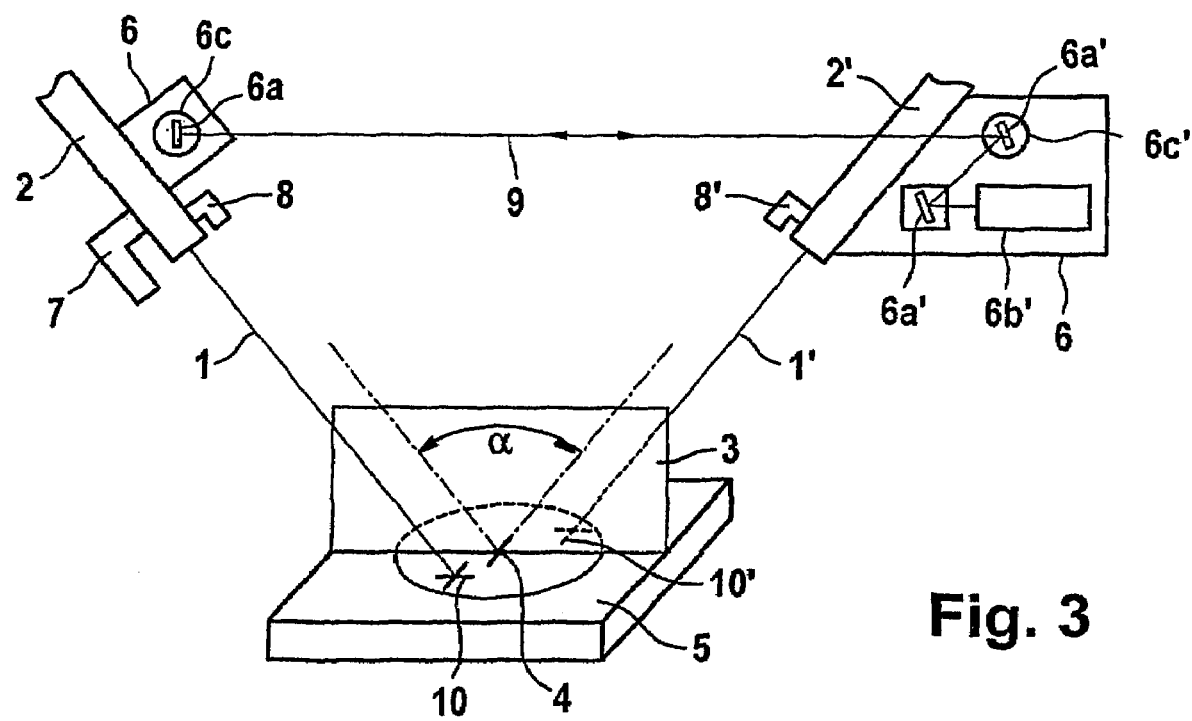

METHOD AND SYSTEM FOR SYNCHRONISING ANGLES

The present invention relates to a method and a system for synchronizing angles of at least two displaceable working means at a predetermined shared point of action. The working means may be robot-controlled tools or radiation emitters or receivers of X-rays, for example.

BACKGROUND

In developing, manufacturing, and testing today's products, high demands are placed on the technologies used to achieve the desired manufacturing accuracy. Products of this type for which the demands on production accuracy are very high include, for example, turbine engines. In particular in the area of manufacturing and testing technology, the positionability of tools or measuring instruments, for example, X-ray diffractometers, with respect to the components is of decisive importance. To achieve high product quality and make manufacturing processes cost-effective, the synchronization of working means displaceable in different manners in an operation is important in particular. It is achieved by determining time intervals, distances, and angles between and during the actions of the particular displaceable working means.

In the cooperation of different working means, the synchronization of the angles between these two working means (angle synchronization) is of particular importance. Typical six-axis robots for controlling working means in production achieve an absolute accuracy of ±0.5 mm in their own coordinate systems when moving to a point, and an angular accuracy of ±0.03°. This accuracy was previously impossible to achieve in spatial synchronization of multiple robots, since the robots' own coordinate systems are difficult to adjust to each other. When highly accurate movements of two robots are required by the manufacturing technology, typically a chain of movements is implemented via a stationary transfer point. This, however, requires time and, in the case of direct cooperation of two working means, for example, in the case of radiation emitters and receivers adjusted to each other, cannot be achieved using robots. Therefore, highly accurate production and measuring systems are usually constructed from fixed linear and rotary axes. Systems having such a conventional structure are, however, less flexible and require more complex maintenance than robot-controlled systems.

SUMMARY OF THE INVENTION

An object of the present invention is therefore to propose a highly accurate angle synchronization of at least two displaceable working means.

The object of the present invention is therefore to propose a highly accurate angle synchronization of at least two displaceable working means.

The present invention provides that the directions of action of the working means, i.e., devices, in particular represented continuously, are detected and united at a predefined point of action, the angle between the directions of action of the working means being determined by an angle measurement, in particular optical angle measurement, and set at a predefined value. Since the directions of action for each of the working means to be synchronized may be represented, for example, by a continuous projection of the directions of action, the directions of action of the working means may be combined at a certain point in space (point of action) with high accuracy and thus the coordinate systems may be adjusted to each other. An accuracy of ±0.01 mm may thus be achieved in the shared coordinate system. By measuring the angle between the working means directly, the exact angle may be determined in the shared coordinate system and set at a desired value. According to the present invention, this takes place via a controller, which detects the measured quantities, in particular the directions of action of the working means, which are represented, for example, by a projection on the surface of the component and recorded by cameras having an associated image processing system, and which detects angles between the directions of action to calculate the relative positions of the directions of action of the tools therefrom and, if needed, to iteratively readjust them via appropriate actuating commands to the actuators or robots of the displaceable working means. A highly accurate angle synchronization of ±0.001° may thus be achieved in the shared coordinate system.

To make a simple and accurate determination of angles possible, in a preferred variant of the method according to the present invention, the angle measurement is performed in a plane which is precisely defined for each working means with respect to its direction of action. This may be achieved in particular in an optical measuring process by aligning an angle measuring device installed on a working means to the direction of action of the particular working means. It is advantageous in particular if the angle is measured in the plane defined by the directions of action of the working means united at the point of action or in a plane parallel thereto because in that case the angle measurement directly defines the angle between the relevant directions of action in the shared plane of action of the working means. This plane of action is important in particular in the case of radiation emitters and receivers adjusted to each other.

In a simple option for optical angle determination, the angle is measured by detecting a light beam transmitted by one of the working means to the other working means and reflected back. This measuring method results in a high relative accuracy in determining the angle and the angle of action. Two rotary adjusting devices may be used for this purpose in particular, which are each installed on one working means in a definite manner, at least one rotary adjusting unit positioning a mirroring surface, for example, a mirror, for reflecting the light beam.

According to the present invention, the reflected light beam may be detected using an autocollimator and/or at least one interferometer having a retroreflector. The deviation of the reflected beam may also be measured using the retroreflector-interferometer. The use of two interferometers each having a retroreflector may also be advantageous for additionally measuring the deviation of the reflected beam.

To represent the direction of action of a working means, according to the present invention a first and a second flat beam which intersect in the direction of action of the working means and yield a cross, for example, in the projection on the component may be formed in particular from visible light, for example, using laser line generators. It may be advantageous to position rotating transparent disks or parallelepipeds in the beam path of the flat beams (laser line) generated by the laser line generators. Due to the resulting alternating parallax offset, the speckle effects occurring when illuminating diffusely reflecting rough surfaces may be drastically reduced because, according to Huygens's principle, roughness peaks serve as starting points for new elementary waves which propagate and move in space in a purely random manner. In generating two flat beams or light planes which intersect in the direction of action of the working means, it is possible to position their light sources outside the line of action of the working means and still continuously represent the direction of action of the working means. For this purpose, both light sources for generating the flat beams and the working means are adjusted accordingly in such a way that the straight line of intersection of the flat beams coincides with the direction of action of the working means.

For the sake of simplicity, the point of action may be marked on a component itself, for example, by a cross, which may be projected, fixedly predefined on the component or otherwise marked. To monitor whether the directions of action of all parts are united at the point of action, it may be established using a camera, for example, whether the cross marking the point of action is made to coincide with the crosses representing the directions of action.

The present invention also relates to a system for angle synchronization using two displaceable working means, in particular robot-controlled tools or robot-controlled emitters and/or receivers of radiation, for example, of X-rays, at a point of action, using which the above-described method may be performed. For this purpose, each of the working means has a device for representing its direction of action. Furthermore, an angle measuring system, in particular an optical angle measuring system, is provided for measuring the angle between the directions of action of the first working means and the second working means. Angle synchronization is achieved using a device for uniting the directions of action of the first working means and the second working means at the point of action and for checking the angle between the directions of action. According to the present invention, this device may be provided in the form of a controller, which identifies the laser crosses which indicate the direction of action of the working means on the surface of the component using an image processing system, optically measures the angle between the working units, calculates the relative position of the directions of action of the working means by linking all detected measured quantities, and, if needed, readjusts them via appropriate actuating commands to the actuators or robots of the displaceable working means.

According to the present invention, the angle measuring system may have a beam guide from one working means to the other working means, the direction of action of each working means running in particular in the plane defined by the beam guide or a plane parallel thereto. In a simple embodiment, the angle measuring system on at least one working means has a mirror or a similar mirroring surface situated on a rotary adjusting device. The controller may then accurately determine the angle between the working means from the rotary setting. For that purpose, according to the present invention, an autocollimator and/or an interferometer having a retroreflector may be provided on at least one working means.

According to a preferred embodiment of the system according to the present invention, the device for representing the direction of action of the working means may have two light sources for generating flat beams, which intersect in the direction of action of the working means. Furthermore, a camera system for recording the projection of the beams and of the point of action may be provided to check the superposition of the beams for representing the direction of action of the working means and the point of action, for example, via image processing.

BRIEF DESCRIPTION OF THE DRAWINGS

Further advantages, features and possible applications of the present invention are derived from the following description of an exemplary embodiment and from the drawing without being limited thereto.

FIG. 1 schematically shows the system according to the present invention for angle synchronization in a three-dimensional view;

FIG. 2 schematically shows the positions of the directions of action of the working means in the system according to FIG. 1, and FIG. 3 shows the angle measuring system for angle synchronization according to the present invention in detail.

DETAILED DESCRIPTION

According to FIG. 1, the system for angle synchronization has two working means 2, 2', which are mounted on six-axis robots 11, 11'. Directions of action 1, 1' of working means 2, 2' are to be united at a shared point of action 4 on component 5. They are to form an angle α. Directions of action 1, 1' are to run in shared plane of action 3. Directions of action 1, 1' of working means 2, 2' united at point of action 4 on component 5 at angle α may be seen in detail in the three-dimensional view of FIG. 2. An optical angle measuring system 6 is situated on working means 2, 2' for determining angle α.

Directions of action 1, 1' being united, as made visible on component 5, may be monitored with the aid of a camera 7, which may be mounted on a working means 2 and is connected to an image analyzing system which optionally readjusts robots 11, 11' for aligning working means 2, 2'.

Angle measuring system 6 and the alignments of directions of action 1, 1' are described in detail below with reference to FIG. 3.

Angle measuring system 6 forms a beam guide 9 between its components mounted on each working means 2, 2'. For this purpose, a rotary adjusting device 6c' having a mirror 6a' is provided on working means 2, the rotary adjusting device communicating with a corresponding rotary adjusting device 6c, having a mirror 6a, situated on the other working means 2'. Both rotary adjusting devices 6c, 6c' are situated with respect to directions of action 1, 1' in such a way that beam guide 9 and directions of action 1, 1' are in the same plane or in parallel planes. Another mirror 6a' is provided on working means 2 to deflect the beam guided in beam guide 9 between working means 2, 2' into an autocollimator 6b'. Using autocollimator 6b' and rotary adjusting devices 6c, 6c' beam guide 9 may be adjusted in such a way that the beam reflected back and forth is imaged therein. From the settings of rotary adjusting devices 6c, 6c', a conclusion may be drawn about angle α between directions of action 1, 1' of the working means because directions of action 1, 1' relative to angle measuring system 6 are known.

For the angle synchronization of directions of action 1, 1', directions of action 1, 1' are represented using devices 8, which are mounted on working means 2, 2'. For this purpose, each device 8 has two light sources for generating flat beams whose beam planes intersect. The straight line of intersection of these two beam planes is adjusted with the aid of device 8 to coincide with direction of action 1, 1' of component 2, 2', so that direction of action 1, 1' is visible and is projected in the form of a cross onto the surface of component 5. The instantaneous positions of the crosses generated via projection 10, 10' of directions of action 1, 1' on component 5 are detected by camera 7 and united at point of action 4 for angle synchronization as described above. Since directions of action 1, 1' are continuously represented using devices 8, continuous synchronization of working means 2, 2' may be easily handled in this way.

The design of faster, more maintenance-friendly production and measuring systems using highly accurate angle synchronization, which are considerably more flexible than conventional systems having fixed linear and rotary axes which were previously required for achieving high synchronization accuracy, thus becomes possible.

What is claimed is:

1. A method for angle synchronization of at least two displaceable working devices comprising:
   detecting directions of action of the working devices, and uniting the directions of action at a predefined point of action, an angle between the directions of action of the working devices being determined by an angle measurement and set at a predefined value.

2. The method as recited in claim 1 wherein the angle measurement is performed in a plane defined for each working device defined with respect to a respective direction of action.

3. The method as recited in claim 1 wherein the angle is measured by detecting a light beam transmitted by one of the working devices to the other working device and reflected back.

4. The method as recited in claim 3 wherein the reflected light beam is detected using an autocollimator and/or at least one interferometer having a retroreflector.

5. The method as recited in claim 1 wherein to represent the direction of actions of the working devices, a first and a second flat beam are formed and intersect in the direction of actions of the working devices.

6. The method as recited in claim 5 wherein the first and second flat beams are from visible light.

7. The method as recited in claim 1 wherein the point of action is marked on a component.

8. The method as recited in claim 7 wherein the point of action is marked by a cross.

9. The method as recited in claim 1 wherein the working devices are robot-controlled tools or robot-controlled radiation emitters and/or receivers at the predefined point of action.

10. The method as recited in claim 1 wherein the directions of action are represented continuously.

11. The method as recited in claim 1 wherein the angle measurement is an optical angle measurement.

12. A system for performing the method as recited in claim 1 comprising:
   a first working device and a second working device, each of the first and second working devices having a device for representing a direction of action;
   an angle measuring system for measuring the angle between the directions of action of the first working device and the second working device; and
   a device for uniting the directions of action of the first working device and the second working device at the point of action and for checking the angle between the directions of action.

13. A system for angle synchronization comprising:
   a first working device and a second working device, each of the first and second working devices having a device for representing a direction of action;
   an angle measuring system for measuring the angle between the directions of action of the first working device and the second working device; and
   a device for uniting the directions of action of the first working device and the second working device at the point of action and for checking the angle between the directions of action.

14. The system as recited in claim 13 wherein the angle measuring system has a beam guide from the first working device to the second working device.

15. The system as recited in claim 14 wherein the direction of action of each of the first and second working devices runs in the plane defined by the beam guide or a plane parallel thereto.

16. The system as recited in claim 14 wherein the angle measuring system on the first working device has a mirror or a mirroring surface situated on a rotary adjusting device.

17. The system as recited in claim 13 wherein an autocollimator ($6b'$) and/or an interferometer having a retroreflector is provided on the first working device.

18. The system as recited in claim 13 wherein the device for representing the direction of action of the first and second working devices has two light sources for generating flat beams, which intersect in the direction of actions.

19. The system as recited in claim 18 wherein the device for representing further includes a camera system for recording the projection of the beams and of the point of action.

20. The system as recited in claim 18 wherein the working devices are robot-controlled tools or robot-controlled radiation emitters and/or receivers at the predefined point of action.

21. The system as recited in claim 18 wherein the angle measurement is an optical angle measurement.

* * * * *